United States Patent
Appel et al.

(10) Patent No.: US 6,437,174 B1
(45) Date of Patent: Aug. 20, 2002

(54) METHOD FOR PRODUCING 2-FLUORO-ISOBUTYRIC ACID ESTERS

(75) Inventors: Wolfgang Appel; Sergej Pasenok, both of Kelkheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/214,219

(22) PCT Filed: Jul. 2, 1997

(86) PCT No.: PCT/EP97/03473

§ 371 (c)(1),
(2), (4) Date: Mar. 29, 1999

(87) PCT Pub. No.: WO98/01416

PCT Pub. Date: Jan. 15, 1998

(30) Foreign Application Priority Data

Jul. 5, 1996 (DE) ......................................... 196 27 150

(51) Int. Cl.$^7$ ................................................ C07C 69/63
(52) U.S. Cl. ...................................................... 560/227
(58) Field of Search ........................................ 560/227

(56) References Cited

U.S. PATENT DOCUMENTS

| 4,523,947 A | 6/1985 | Szczepanski et al. |
| 5,095,113 A | 3/1992 | Chiang et al. |

FOREIGN PATENT DOCUMENTS

| EP | 0 506 059 A2 | 9/1992 |
| WO | WO 97/08156 | 3/1997 |
| WO | WO 98/15537 | 4/1998 |

Primary Examiner—Paul J. Killos
(74) Attorney, Agent, or Firm—Frommer Lawrence & Haug LLP

(57) ABSTRACT

The present invention concerns a method for producing esters of 2-fluoro-iso butyric acid in which the corresponding 2-hydroxyisobutyric acid ester is reacted with hydrofluoric acid.

5 Claims, No Drawings

METHOD FOR PRODUCING 2-FLUORO-ISOBUTYRIC ACID ESTERS

The present invention relates to a process for the preparation of esters hydrogen flouride or of 2-fluoroisobutyric acid. In particular, the present invention relates to an economically and ecologically advantageous process for the preparation of these esters, hydrogen fluoride or hydrofluoric acid (HF) being used as fluorinating agent.

2-fluoroisobutyrates are of great interest as intermediates for the preparation of industrially useful triazine herbicides. Such a triazine herbicide is described, for example, in WO 90/09378:

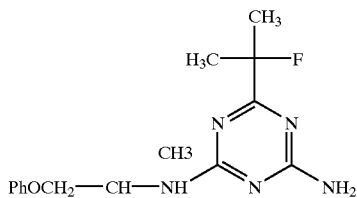

These triazine herbicides are prepared, for example, by reacting the corresponding bigunanide precursor with 2-fluoroisobutyrates.

A number of methods for the synthesis of 2-fluoroisobutyrates are described in the literature. According to J. Org. Chem. 33, 4279 (1968), the fluoroisobutyrate can be prepared by reacting the bromoisobutyrate with AgF. The yields are, however, low since the main product is formed by elimination of the methacrylate, and, in any case, the costs of AgF make the method commercially insignificant.

According to a second process (J. Org. Chem. 55, 3423 (1990)),

With this process as well, the yield is low, both stages must be carried out at low temperature (−78° C. and −40° C.), and the handling of elemental fluorine is problematic. One method, which likewise starts from silyl enol ether, is not suitable industrially because of the hazardous fluorinating agent (hypofluorite) and the requisite low temperature (Du Pont, U.S. Pat. No. 4,215,044).

According to a patented process (Idemitsu Kosan, JP 05043515-A), the preparation of 2-fluoroisobutyrates is described starting from methacrylates, and their reaction with HF/amine reagents in the presence of Lewis acids. The yields achieved therewith are, however, below 20%.

In another patent (Idemitsu Kosan, JP 3240-764-A), acetone cyanohydrin is firstly converted into the corresponding methanesulfonate. Reaction with KF in diethylene glycol then gives 2-fluoro-2-methylpropionitrile in very moderate yields (12.2%).

The literature describes a number of synthetic methods starting from α-hydroxy esters which produce α-fluorinated esters using extraordinarily expensive reagents such as dimethylaminosulfur trifluoride (ICI, EP 468 681), (2-chloro-1,1,2-trifluoroethyl)diethylamine (Yarovenko Reagens) (Isr. J. Chem. 8, 925–933 (1970)) or N-fluoropyridinium salts (Onoda Cement, JP 2 207 228). The yields are, however, only moderate in the case of α,α-disubstituted hydroxy esters such as hydroxyisobutyrates due to acrylate formation, and the methods are too expensive for industrial processes because of the type of reagents used.

Two more recent patented methods each use 2-hydroxyisobutyrates as starting materials. In the first case (Idemitsu Kosan, EP 506 059 A2/U.S. Pat. No. 5,175,345), the starting material is reacted with fluorosulfonic acid with or without the addition of a HF source, good yields only being obtained when the HF source (HF/pyridine: 70/30) is added and after long reaction times (18 hours).

In the second case (Idemitsu Kosan, WO 9424086-A1), the 2-hydroxyisobutyrate is firstly carefully reacted with an excess of thionyl chloride. In a second stage, this reaction mixture is then added dropwise, at a low temperature (−10° C. to −78° C.), to a large excess of anhydrous

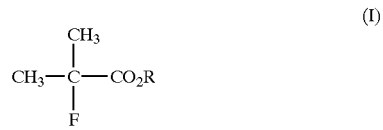

(I)

where R is methyl, ethyl, n-propyl, i-propyl, n-butyl, i-butyl, sec-butyl and tert-butyl, or is phenyl, according to which the corresponding 2-hydroxyisobutyrate is reacted with hydrogen fluoride or hydrofluoric acid as fluorinating agent at a temperature between 0° and 80° C.

As already mentioned above, there are two industrial processes which start from the starting material also used here. Replacement of the hydroxyl group for the fluorine atom is achieved in this case by reaction with fluorosulfonic acid in the presence of a HF/amine mixture or in the two-stage process with thionyl chloride and HF.

Surprisingly, it has now been found that in choosing a suitable temperature, this reaction can also be carried out easily with a hydrofluoric acid, preferably with anhydrous HF (hydrogen fluoride), without the need for further additives, in a short reaction time, to give high yields. The process according to the invention has the additional advantage that the methacrylate byproduct which can only be separated off with difficulty is only produced in a very small amount.

The process according to the invention is also ecologically advantageous: the HF used as fluorinating agent and solvent can be recycled by simple distillation after the reaction since no additives are necessary.

To carry out the reaction, 2-hydroxyisobutyrate is reacted with a 10–80-fold molar excess, preferably 20–70-fold molar excess of hydrogen flouride or hydrofluoric acid at 0–80° C., preferably 20–75° C. and particularly preferably at 30–60° C., in an autoclave. The reaction time is usually 3–12 hours, and the mixture is preferably allowed to react for 4–7 hours. If the process is carried out at low temperatures, e.g. at 30° C. and below, a longer reaction time may be expedient to increase the yield.

The reaction usually proceeds under autogeneous pressure. Afterwards, the excess of hydrofluoric acid can simply be distilled off.

Workup is by customary methods known to the person skilled in the art, by, for example, adding the residue to an ice/water mixture and extracting the product with a suitable solvent, e.g. ethyl acetate, methylene chloride or ether. The product, the 2-fluoroisobutyrate, may then be expediently obtained by distillation.

The process according to the invention allows the desired product to be advantageously prepared in one stage in high yield.

The following examples serve to illustrate the process according to the invention without, for example, limiting it thereto.

EXAMPLES

1) Ethyl 2-fluoroisobutyrate

A 300 ml pressure vessel made from stainless steel, which has been precooled in an ice bath, is charged with 160 g (8 mol) of anhydrous HF, and then 35 g (0.27 mol) of ethyl 2-hydroxyisobutyrate are added. The reaction vessel is closed, and the contents are heated at 50° C. for 5 hours. The reactor is then cooled to 25° C. and decompressed via a cold trap, the excess HF distilling into the cold trap. When no more HF passes over, the pressure vessel is cooled in an ice bath, then opened, and the reaction mixture is carefully poured onto 200 g of ice/water. The aqueous product phase is extracted twice with methylene chloride, and the extract is washed once with water and The results of these examples are shown together with Examples 1 and 2 in Table 1.

The results given in Table 1 clearly show the influence of the parameters temperature, reaction time and molar ratio of the reactants on the reaction. By appropriate choice of the parameters, the reaction can be controlled specifically in favor of conversion and/or selectivity.

What is claimed is:

1. A process for the preparation of 2-fluoroisobutyrates of the formula (1)

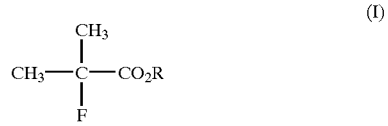

where R is methyl, ethyl, n-propyl, i-propyl, n-butyl, i-butyl, sec-butyl and tert-butyl or phenyl, which comprises reacting the corresponding 2-hydroxyisobutyrate with hydrogen fluoride or hydrofluoric acid as fluorinating agent at a temperature between 0° and 80° C.

| Ex. No. | Starting material A, B | Amount g | HF g | Time h | Temp. ° C. | Conversion % | Product % | Acrylate % |
|---|---|---|---|---|---|---|---|---|
| 1 | A | 35 | 160 | 5 | 50 | 95 | 94 | 6 |
| 2 | B | 15 | 100 | 72 | 30 | 99 | 95 | 5 |
| 3 | A | 5 | 60 | 3.5 | 80 | 100 | 46 | 54 |
| 4 | A | 10 | 70 | 4 | 60 | 97 | 87 | 13 |
| 5 | A | 10 | 110 | 4 | 50 | 89 | 92 | 8 |
| 6 | A | 10 | 80 | 22 | 20 | 23 | 100 | — |
| 7 | A | 10 | 80 | 72 | 20 | 42 | 98 | 2 |
| 8 | A | 10 | 80 | 25 | 30 | 55 | 98 | 2 |
| 9 | B | 10 | 30 | 4 | 50 | 62 | 90 | 10 |
| 10 | B | 10 | 80 | 4 | 50 | 98 | 91 | 9 |
| 11 | B | 10 | 80 | 18 | 30 | 85 | 94 | 6 |

Starting material A: Ethyl 2-hydroxyisobutyrate
Starting material B: Methyl 2-hydroxyisobutyrate
"Acrylate": Methyl methacrytate 2. The process as claimed in claim 1, wherein the molar ratio of hydrogen fluoride to 2-hydroxyisobutyrate is between 10 and 80.

3. The process as claimed in claim 2, wherein the molar ratio of hydrogen fluoride to 2-hydroxyisobutyrate is between 20 and 70.

4. The process as claimed in claim 1, wherein the reaction is carried out at a temperature between 20° and 75° C.

5. The process as claimed in claim 1, wherein the excess fluorinating agent is distilled off after the reaction.

* * * * *